US012667305B2

(12) United States Patent
Cashman

(10) Patent No.: US 12,667,305 B2
(45) Date of Patent: Jun. 30, 2026

(54) COMBINED TESTING AND TREATMENT UNIT

(71) Applicant: Kathryn Cashman, Nashville, TN (US)

(72) Inventor: Kathryn Cashman, Nashville, TN (US)

( * ) Notice: Subject to any disclaimer, the term of this patent is extended or adjusted under 35 U.S.C. 154(b) by 636 days.

(21) Appl. No.: 17/985,947

(22) Filed: Nov. 14, 2022

(65) Prior Publication Data

US 2023/0277124 A1 Sep. 7, 2023

Related U.S. Application Data

(60) Provisional application No. 63/278,322, filed on Nov. 11, 2021.

(51) Int. Cl.
| *A61B 5/00* | (2006.01) |
| *A61B 5/087* | (2006.01) |
| *A61B 5/097* | (2006.01) |
| *A61M 11/00* | (2006.01) |
| *A61M 15/00* | (2006.01) |

(52) U.S. Cl.
CPC ............ *A61B 5/4839* (2013.01); *A61B 5/087* (2013.01); *A61B 5/097* (2013.01); *A61M 11/005* (2013.01); *A61M 15/0021* (2014.02); *A61B 2560/0431* (2013.01); *A61M 2205/123* (2013.01); *A61M 2230/40* (2013.01)

(58) Field of Classification Search
None
See application file for complete search history.

(56) References Cited

U.S. PATENT DOCUMENTS

| | | | | |
|---|---|---|---|---|
| 6,179,583 B1 * | 1/2001 | Weston | ............. | A61M 5/16809 |
| | | | | 417/462 |
| 2005/0087189 A1 * | 4/2005 | Crockford | .............. | A61M 11/06 |
| | | | | 128/203.15 |
| 2006/0237001 A1 * | 10/2006 | Stangl | .................. | A61M 11/005 |
| | | | | 600/300 |
| 2007/0157931 A1 * | 7/2007 | Parker | .................. | A61M 11/005 |
| | | | | 128/204.23 |
| 2017/0182267 A1 * | 6/2017 | Cameron | ............. | A61M 11/042 |
| 2018/0028441 A1 * | 2/2018 | Cashman | .......... | A61M 15/0065 |
| 2019/0046079 A1 * | 2/2019 | Reed | ................. | A61M 15/0021 |
| 2021/0023315 A1 * | 1/2021 | Goldenberg | ...... | A61M 15/0025 |

* cited by examiner

*Primary Examiner* — Michael R Bloch
(74) *Attorney, Agent, or Firm* — Wayne Edward Ramage; Baker Donelson

(57) ABSTRACT

A combined or convertible handheld unit that combines a personal spirometer, exhalation-analysis or breath-analysis function with a nebulizer or vaporizing function. The nebulizer or vaporizing function includes, but is not limited to, functions provided by devices such as inhalers, nebulizers, vaporizers, humidifiers, ventilators, or other devices that are used for delivery of any sort of substance into the body via breathing, and includes but is not limited to devices that break up solutions and suspensions into small aerosol droplets for inhalation by a user. The unit also performs full exhalation detection and analytics.

10 Claims, 6 Drawing Sheets

COMBINED TESTING AND TREATMENT UNIT

This application claims benefit of and priority to U.S. Provisional App. No. 63/278,322, filed Nov. 11, 2021, which is incorporated herein in its entirety by specific reference for all purposes.

FIELD OF INVENTION

The present invention relates to a system for managing health and related information in connection with use of a personal testing and treatment device or unit, comb inhalation device and a personal breath analysis device. More particular, this invention relates to a computer-based system and applications for managing health and related information through use of a handheld personal device that generates or nebulizes a vapor for inhalation by a user, and that provides exhalation or breath analysis.

BACKGROUND OF INVENTION

Various devices for inhalation, nebulizing or vaporizing functions are known in the prior art, as are devices for breath analysis or measurement of lung function. Examples include those described in Gueret, U.S. Pat. No. 5,529,055 (Jun. 25, 1996); Haber, et al., U.S. Pat. No. 5,435,282 (Jul. 25, 1995); van der Linden, et al., U.S. Pat. No. 5,950,619; Smith, et al., US 2003/0140921 (Jul. 13, 2003); Star, et al., US 2010/0282245 (Nov. 11, 2010); Patton, et al., US 2013/0269694 (Oct. 17, 2013); Kotnik, et al., US 2008/0110452 (May 15, 2008); Albert, et al, US 2015/0014433 (Jan. 15, 2015); Arkush, US 2015/0258370 (Sep. 17, 2015); U.S. patent application Ser. No. 15/699,786 (filed Sep. 8, 2017); and Sakurada, et al., US 2010/0089394 (Apr. 15, 2010); all of which are incorporated herein in their entireties by specific reference for all purposes.

Sakurada discloses an inhaler capable of measuring lung function, but the lung function measurement uses the same components and fluid passageway as the inhaler, thereby allowing cross-contamination and interference between the two functions.

SUMMARY OF INVENTION

In various exemplary embodiments, the present invention comprises a combined or convertible handheld unit that combines a personal spirometer, exhalation-analysis or breath-analysis function with a nebulizer or vaporizing function. The nebulizer or vaporizing function includes, but is not limited to, functions provided by devices such as inhalers, nebulizers, vaporizers, humidifiers, ventilators, or other devices that are used for delivery of any sort of substance into the body via breathing, and includes but is not limited to devices that break up solutions and suspensions into small aerosol droplets for inhalation by a user. In several embodiments, the unit also performs full exhalation detection and analytics.

Use and management of the unit may be coordinated with a computer-based program or application, which can run on a mobile computing device or other computing device. In various embodiments, the present invention comprises and uses the unit as apart of a computer-based system for receiving, analyzing, processing, managing and sending personal health information, and other information in conjunction with use of one or more personal nebulizer or vaporizing devices and personal breath analysis, exhalation analysis, or spirometer devices. In several embodiments, the system comprises a health or wellness computer application, program or database on a computer or mobile device (e.g., smart phone, tablet computer), which can coordinate collecting, storing, analyzing, and diagnosing various information obtained from a variety of other devices or sources, such as a breath analysis device that can capture and analyze the content of exhaled air, a health band (e.g., Fit Bit), other detection devices, or information entered into and stored in a separate health or wellness computer application, program or database on a computing device or mobile computing device. The system can use this information to develop health-related recommendations for an individual, including, but not limited to, recommendations for a substance or substances to be used in a personal vaporization device. Further, a particular breath analysis, when completed, the system real-time stamps the location (using GPS of the device) to gather a variety of relevant information about the location at that time, including, but not limited to, environmental factors, allergens present, weather, elevation, humidity, air quality index, and other similar factors. This information is then used to properly dose the user/patent for the current or next round of treatment.

DETAILED DESCRIPTION OF EXEMPLARY EMBODIMENTS

Figure 1B:
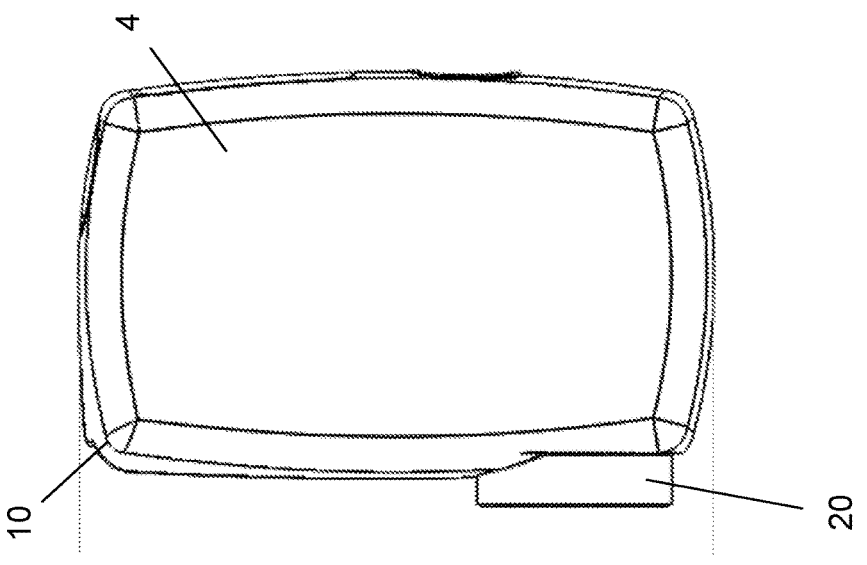
FIG. 1B shows a side view of the device of FIG. 1A.

In various exemplary embodiments, the present invention comprises a combined or convertible handheld unit 2 that combines a personal spirometer, exhalation-analysis or breath-analysis function with a nebulizer or vaporizing function. The nebulizer or vaporizing function includes, but is not limited to, functions provided by devices such as inhalers, nebulizers, vaporizers, humidifiers, ventilators, or other devices that are used for delivery of any sort of substance into the body via breathing, and includes but is not limited to devices that break up solutions and suspensions into small aerosol droplets for inhalation by a user. In several embodiments, the unit also performs full exhalation detection and analytics.

Use and management of the unit may be coordinated with a computer-based program or application, which can run on a mobile computing device or other computing device. In various embodiments, the present invention comprises and uses the unit as apart of a computer-based system for receiving, analyzing, processing, managing and sending personal health information, and other information in conjunction with use of one or more personal nebulizer or vaporizing devices and personal breath analysis, exhalation analysis, or spirometer devices. In several embodiments, the system comprises a health or wellness computer application, program or database on a computer or mobile device (e.g., smart phone, tablet computer), which can coordinate collecting, storing, analyzing, and diagnosing various information obtained from a variety of other devices or sources, such as a breath analysis device that can capture and analyze the content of exhaled air, a health band (e.g., Fit Bit), other detection devices, or information entered into and stored in a separate health or wellness computer application, program or database on a computing device or mobile computing device. The system can use this information to develop health-related recommendations for an individual, including, but not limited to, recommendations for a substance or substances to be used in a personal vaporization device. Further, a particular breath analysis, when completed, the system real-time stamps the location (using GPS of the device) to gather a variety of relevant information about the location at that time, including, but not limited to, environmental factors, allergens present, weather, elevation, humidity, air quality index, and other similar factors. This information is then used to properly dose the user/patent for the current or next round of treatment.

As seen in FIG. 1A-4, the unit 2 comprises an outer main housing or shell 4 with one or more ports or mouthpiece units 10, 20. The housing may be unitary, or multi-part (e.g., a clamshell, with a top and bottom, or right and left sides 4*a,b*, where the parts may be detached from each other, or may be hingedly attached). The mouthpiece unit(s) may be detachable and replaceable. In some embodiments, the detached mouthpiece units(s) may be washable and sanitizable, and thus re-usable.

Figure 1A:
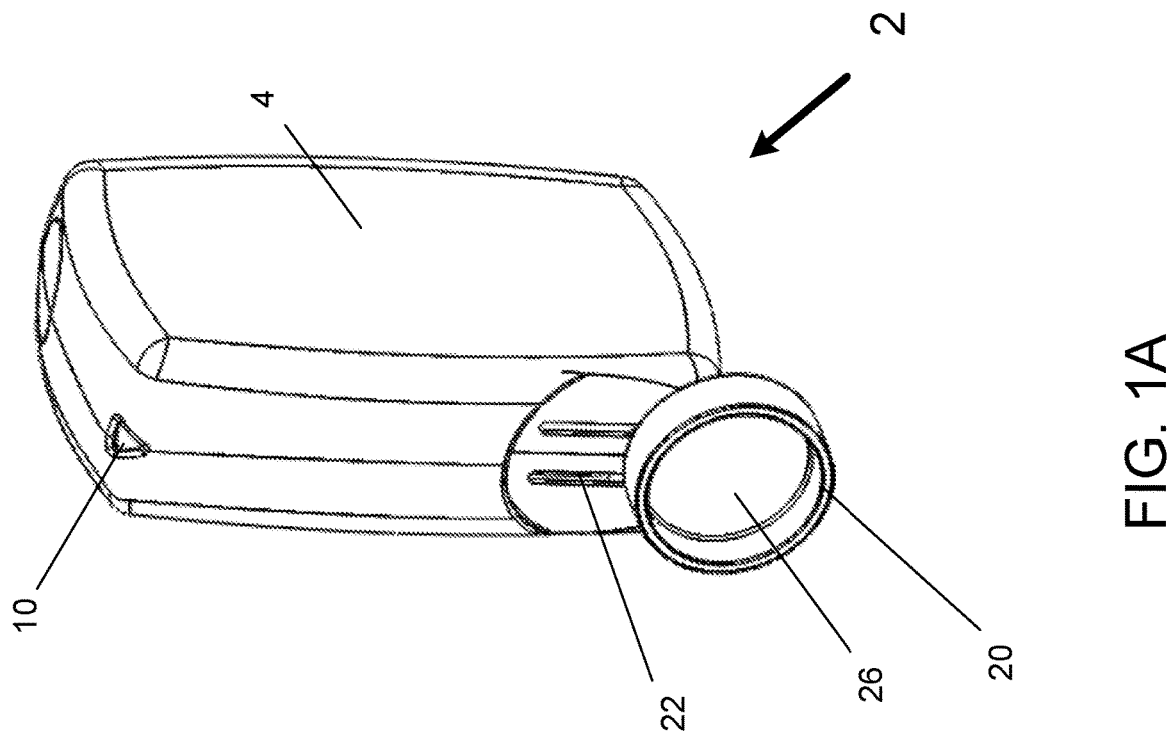
FIG. 1A shows a front perspective view of a device in accordance with an exemplary embodiment of the present invention.

In several embodiments, the unit comprises a single exhalation port 20 into which the user breathes for some form of breath testing, as described further herein. As seen in FIGS. 1A-4, the exhalation port or mouthpiece 20 may be rotatably or slidingly attached to the housing, such as through tabs 24 that extend from the back of the port or mouthpiece 20 into slots 22 in the front of the housing, and then rotated or moved down from a home position, as seen in FIG. 1B, to a use position, as seen in FIG. 1A. The unit then performs various tests or analyses, as described below. The unit may perform a pulmonary function or breathing test (i.e., spirometry) for measuring the volume of air inspired and/or expired by the lungs of the user by pressure or ultrasonic transducers 26, effectively acting as a spirometer. The test identifies, among other things, abnormal ventilation pattern (e.g., obstructive, and restrictive). It also can be used to identify and find the cause of shortness of breath, assessing the effect of medication on lung function, and evaluating progress for treatment of certain types of lung disease or conditions (e.g., asthma, COPD, bronchitis, emphysema, and COVID-19).

In the use position, the user blows into the exhalation port or mouthpiece 20, his or her breath contacts the transducers 26 which are located on the inside of the back of the mouthpiece, and the exhaled air then passes through and exits through holes or openings 28 proximate the edges of the back. The exhaled air passageway is entirely separate from a second passageway used for the inhalation function, as described below. There is no fluid contact between the passageways. The exhaled air enters through its own port, is analyzed, and exits through its own exit ports or openings, separate from the inhalation entrance and exit ports and passageway. In a preferred embodiment, the exhaled air enters through its own port, is analyzed, and exits through its own exit ports or openings without entering the portion of the housing containing the inhalation ports and passageway. The separation prevents the possible contamination of one function by the other, and in particular, prevents elements of the exhaled breath from migrating to or contaminating the inhalation elements and function, while still providing the convenience of having a single device provide both functions.

The housing 4 further includes one or more controls, such as a button, slider, or switch 30 that may be used to turn the unit on or off, or control other functions, as described below. The button may be spring-operated 31 to switch between positions. One or more lights, LEDS, or other indicators 32 may be provided to indicate status of the unit, including, but not limited to, power status and operational status. In the embodiment shown, a LED 32 or other form of light is visible on the outer surface of the shell to indicate power status and breath volume test result. The LED or light 32 indicates when the unit is on, when the user has correctly and properly blown into the exhalation port 20 sufficiently to provide a viable test result, and a color (e.g., Green/Yellow/Red) to indicate qualitatively the results of the breath volume test. The LED or light 32 may also be used to provide similar information for the inhalation function. Other forms of audio and/or visual acknowledgment or indicators may be provided.

Figures 2A, 2B:
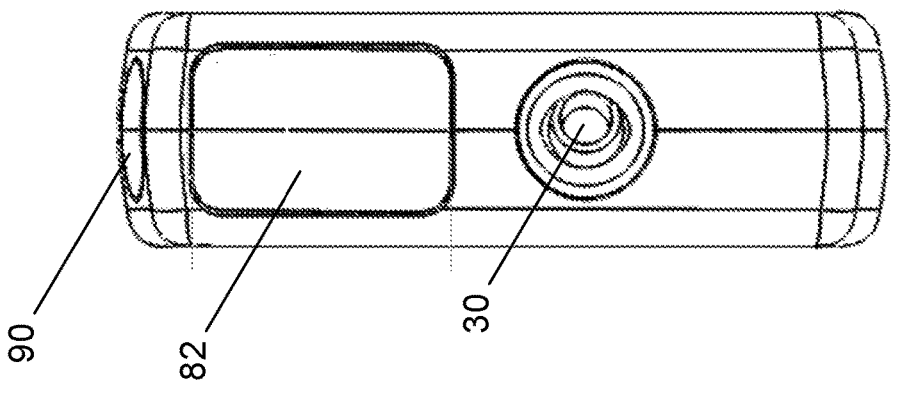
FIG. 2A shows a back view of the device of FIG. 1A.
FIG. 2B shows a back perspective view of the device of FIG. 1A.
Figures 3A, 3B, 3C:
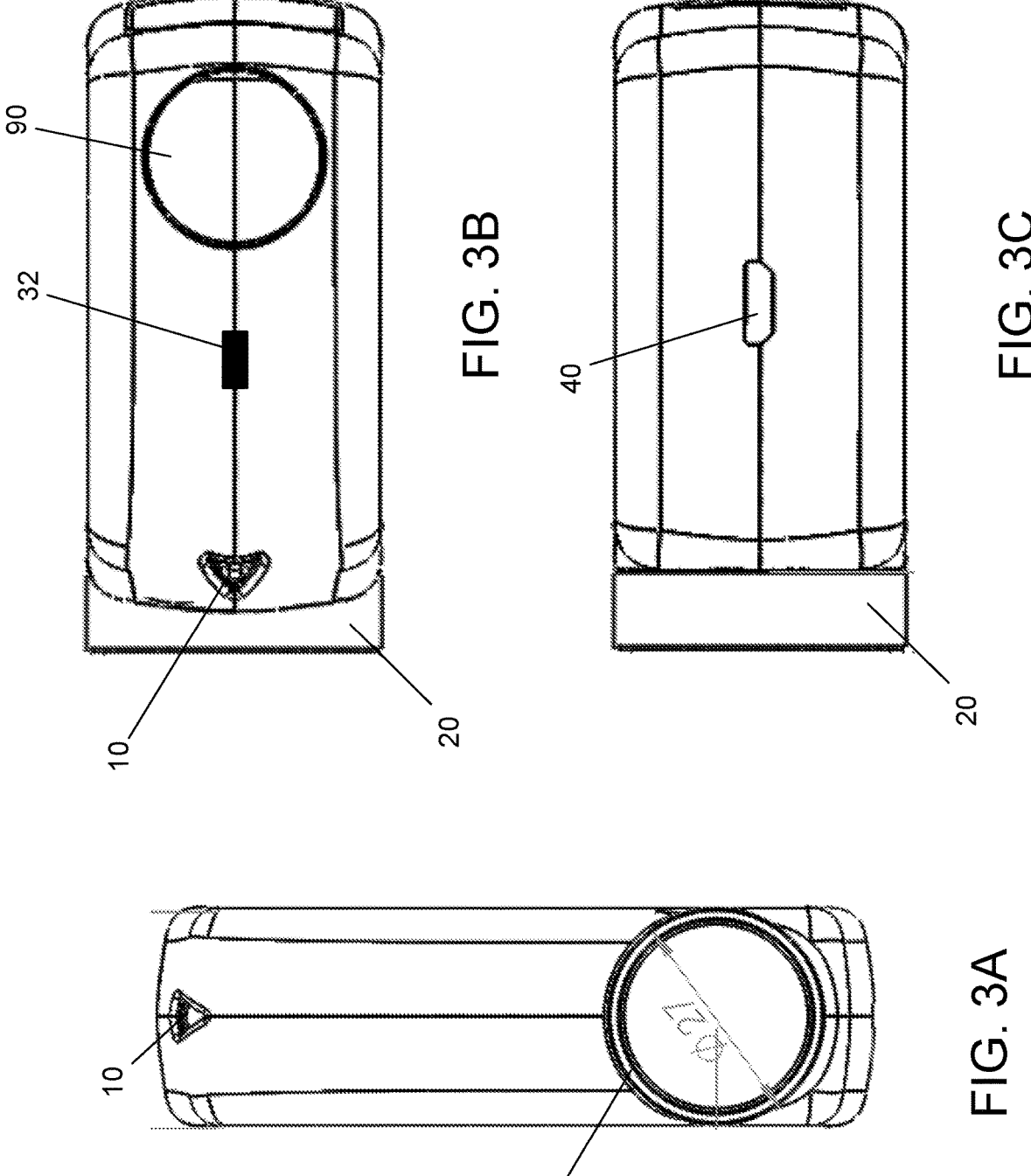
FIG. 3A shows a front view of the device of FIG. 1A.
FIG. 3B shows a top view of the device of FIG. 1A.
FIG. 3C shows a bottom view of the device of FIG. 1A.
Figure 4:
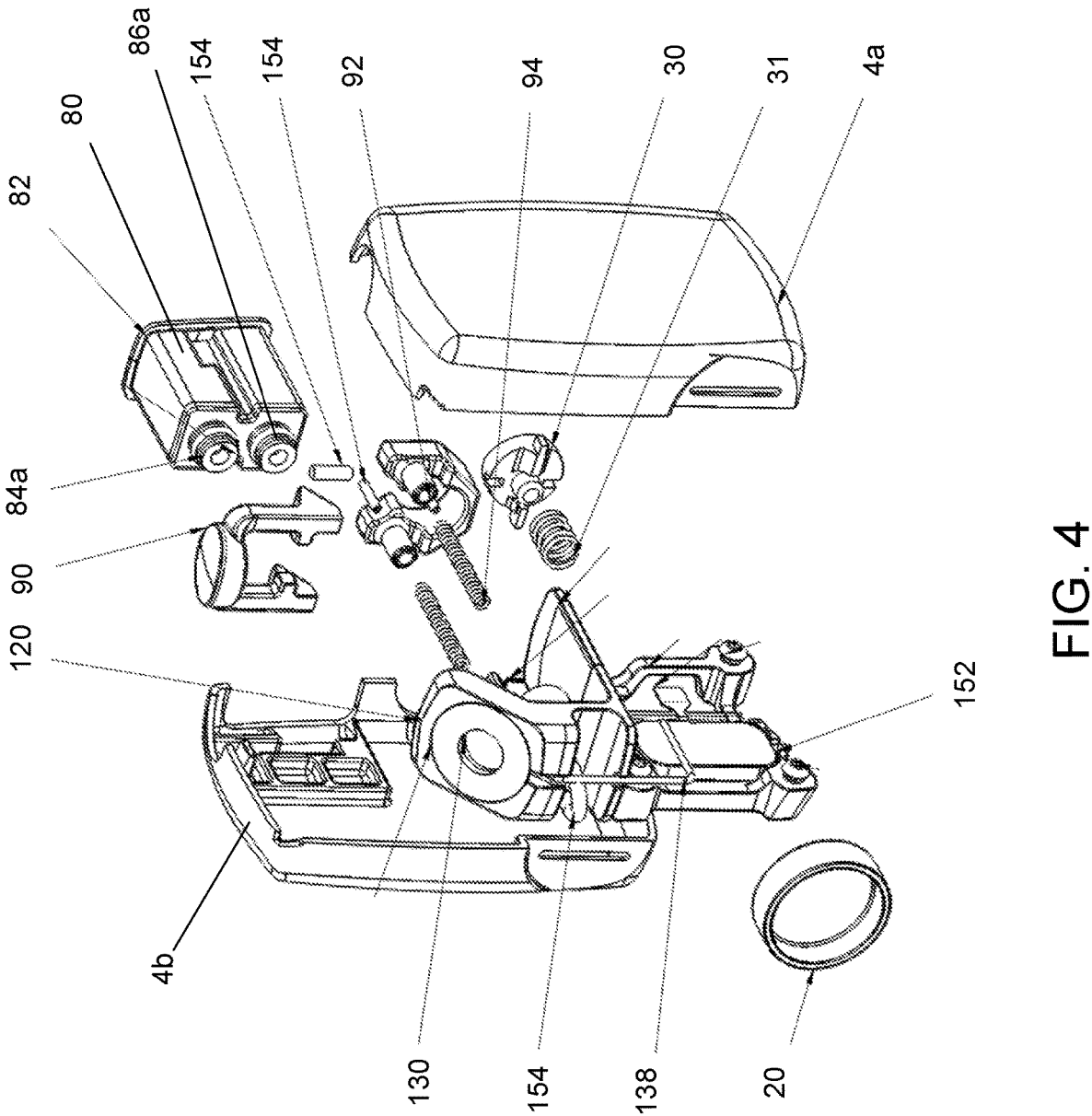
FIG. 4 shows an exploded perspective view of the device of FIG. 1A.
Figure 5:
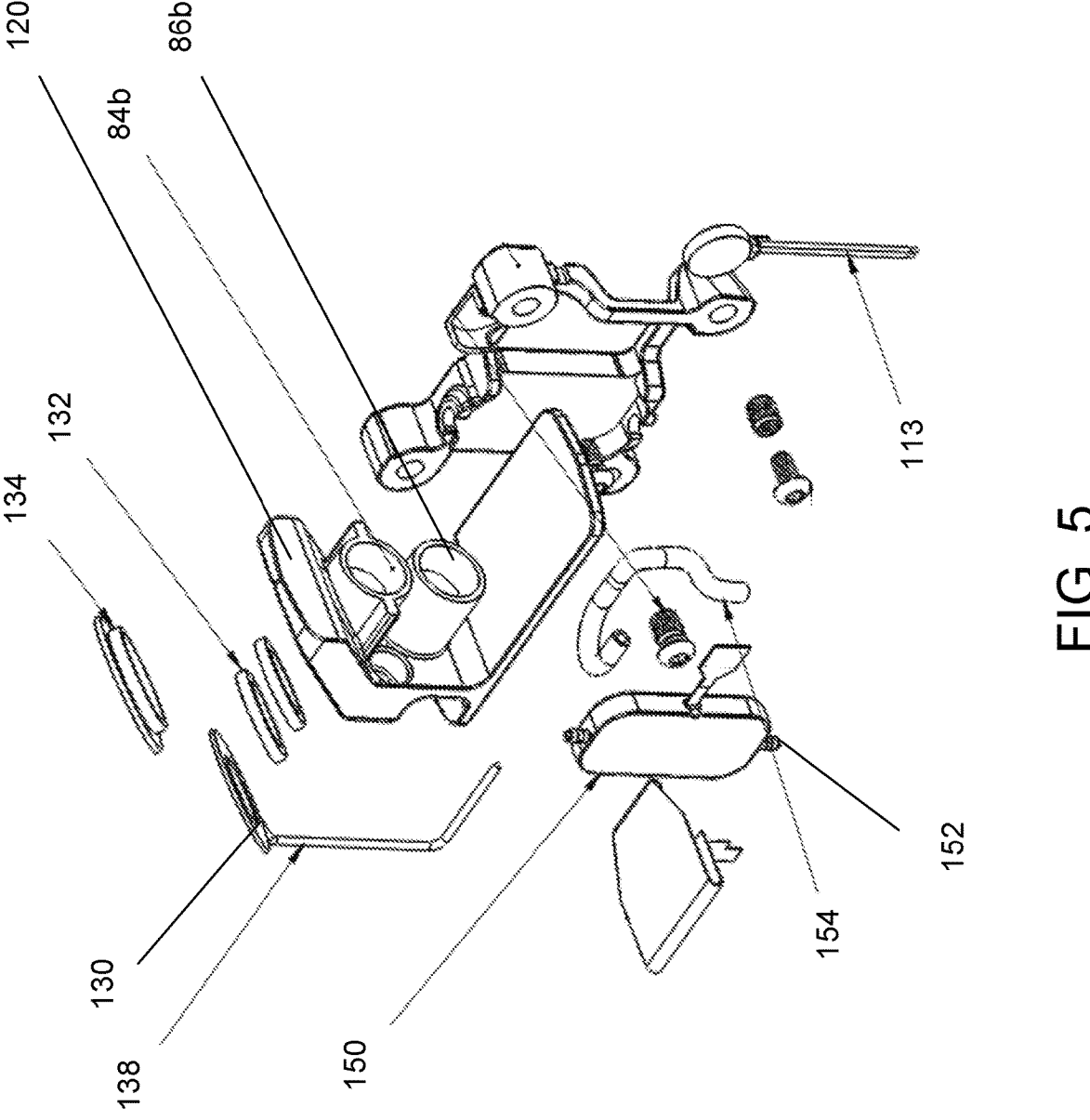
FIG. 5 shows a partial exploded perspective view of internal components of the device of FIG. 1A.
Figures 6A, 6B, 6C:
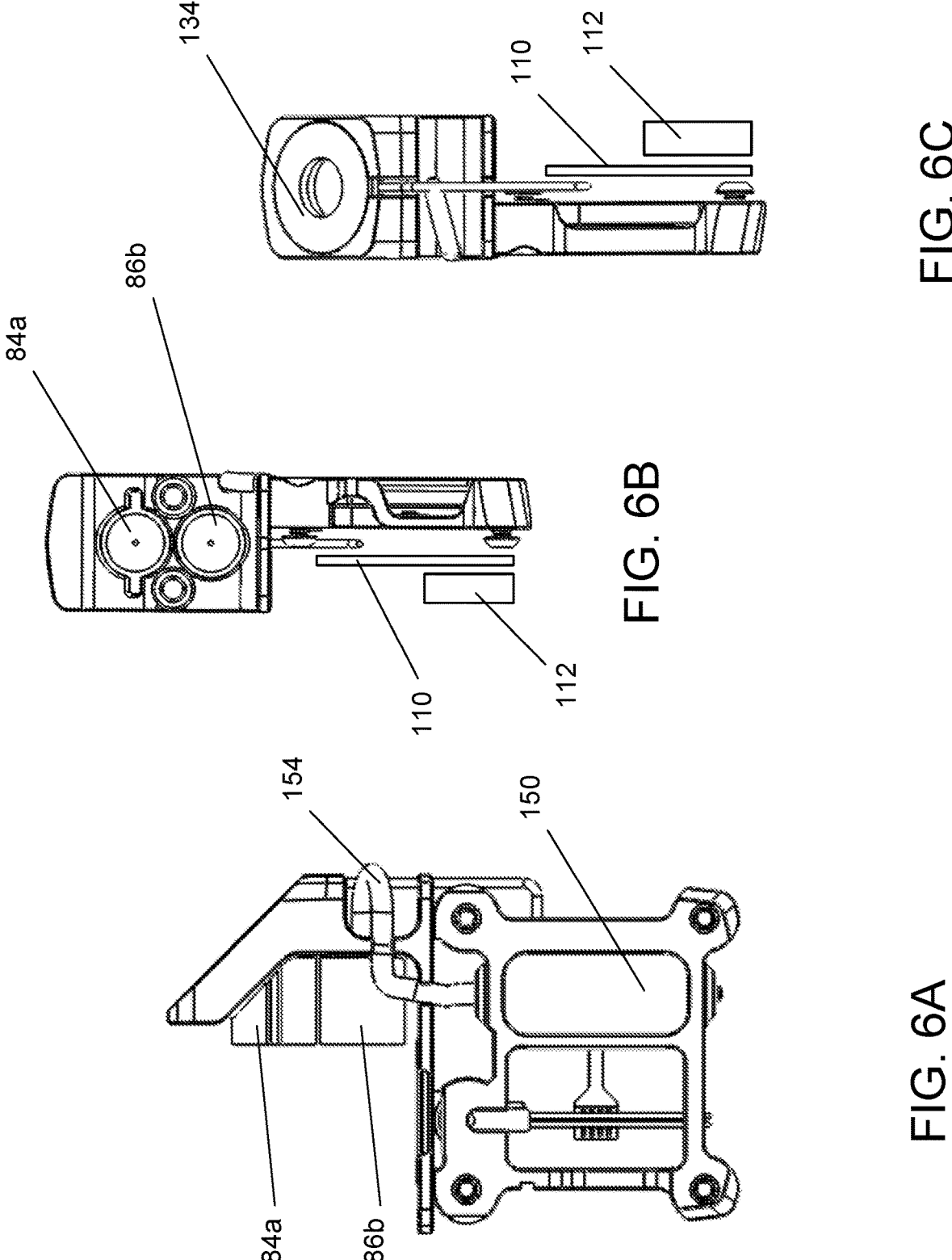
FIG. 6A shows a partial side view of assembled internal components of the device of FIG. 1A.
FIG. 6B shows a back view of the assembled internal components of FIG. 6A.
FIG. 6C shows a front view of the assembled internal components of FIG. 6B.

The main shell further comprises an opening for insertion of a pod, ampoule or cartridge 80 into the unit. The pod, ampoule, or cartridge 80, as seen in FIG. 2B, holds the substance to be vaporized or nebulized during operation of the unit. The vaporized substance is inhaled by the user while holding the unit. When inserted, the surface of the outer end 82 of the pod 80 acts as a cover for the opening and smoothly aligns with the contours of the housing. In some embodiments, a separate cover can be placed over the opening when a pod is not inserted therein.

As seen in the figures, in one embodiment the pod comprises an interior chamber with two ports on the back, one 84*a* above the other 86*a*. The ports extend outward from the pod and comprise an interface and a gasket configured to mate with matching ports 84*b*, 86*b* inside the unit. When inserted, the pod is locked into place by a bracket 92 interacting with arms extending downward from the retention/release button 90. The bracket is under tension by compression of springs 94. When the retention/release button 90 is pressed down, the arms move downward, releasing the bracket 92, which is pushed backward and out from the housing by action of the springs 94. The pod thus is held securely in place, until ejected by means of the release button on the unit.

The pod/ampoule 80 may comprise a wireless chip containing some or all of the following information: pod identification; substance/medicament identification; frequency set; intended user; user age; user weight; activate location; available doses; doses provided to the patient; a timer reminder for the user to take the substance/medicament; whether access is Face ID restricted; and confirmation of the user.

The substance to be vaporized may be in the form of a liquid, gel, gas, solid, or the like. In several embodiments, the substance comprises one or more of a therapeutic substance, homeopathic or naturopathic formulations or remedies, serums, or the like. Particular substances may be chosen or selected for particular desired effects, therapies or treatments, and substances have natural vaporization characteristics that are dependent on a variety of factors, including, but not limited to, temperature, air flow, and substance composition and chemical state. Selection of one or more substances for vaporization may be made based upon information obtained from the breath analysis tests performed by the unit 2, or from other devices or systems, such as a separate breath analysis device that can capture and analyze the content of exhaled air, a health band (e.g., Fit Bit), other detection devices, or information stored in or entered into in a health or wellness computer application, program or database on a computer or mobile device (e.g., smart phone, tablet computer), which can coordinate diagnosing this information and developing recommendations for the substance or substances to be used (as described below).

In an alternative embodiment, the unit comprises an internal, refillable chamber for holding the substance to be vaporized. The refillable chamber may be filled by insertion of the substance through the opening with removable cover, or other filling port.

In one exemplary embodiment, as seen in FIGS. 5 and 6A-C, the interior of the unit comprises an atomization chamber, which receives the substance from the ampoule or refillable chamber through such means as a wick or other conduit. Air enters the entrance port 152 on one end of the peristaltic pump 150, and is directed through tubing 154 to the lower or inlet port(s) 86*a,b* associated with the pod. The substance in the pod is then transmitted out the upper or outlet port(s) 84*a,b*. Vaporization is achieved by means of one or more piezoelectric transducers or atomizers 130, providing sonic or ultrasonic vibration. Transducers are connected 138 to the circuit board and power supply. Vapor is emitted through tubing or conduits to the mouthpiece support orifice 134. Two or more gaskets 132 are located between the transducer 130 and the internal mouthpiece frame 120 Calibration and control of the atomization process (e.g., temperature, size of inlet openings, rate of vaporization, timer) may be controlled by the user manually using a control on the unit, automatically controlled based upon a code or symbol (e.g., bar code) on the ampoule read by a bar code scanner in the device after insertion, or remotely (such as by wireless connection to a computer or mobile device). This calibration and control may be performed according to the diagnosis and recommendations developed in the manner described above.

A circuit board 110 provides control and power functions. Power may be provided by one or more batteries 112. The battery or batteries may be standard, replaceable batteries, or may be a rechargeable battery built into the unit, and recharged with a recharging cord or similar means. In some embodiments, a power cord and plug may be plugged into a standard electrical outlet to provide power. A wireless-network communications (wifi), Near Field Communication (NFC) and/or Bluetooth® chip provides for wireless communications, in conjunction with antenna 113. A USB, mini-USB, or similar communications and/or data port 40 provides for direct communications, and uploading and downloading of programs or data. The USB port or other port 40 may also be used as a power source, and may be used to recharge the rechargeable battery 112. In several embodiments, the unit may use wireless charging or other form of self-inducting charging.

Other vaporization means may be provided, such as a heat source (burner, flame, electrical). Temperature may be controlled in the manner of other parameters discussed above. In several embodiments, the temperature is regulated to keep the substance cool to enhance the stability of the chemical constituents thereof. In yet another embodiment, a unit has multiple vaporization elements, and can vaporize different substances from one or more, or multiple, refillable chambers or multiple ampoules simultaneously, in sequence, or some combination thereof.

The unit may have a computer memory storage capability, and store vaporization treatment data so that the details of the vaporization treatment can be subsequently used to evaluate clinical or medical treatment compliance and effectiveness. The information may be provided by wired or wireless connection to a health or wellness program. The unit may have one or more means of wireless communication and wired/or communication (e.g., data ports, USB ports, telecommunications ports). The unit may transmit information and data to (and received the same from) one or more remote servers and databases, and may be "cloud-based." As mentioned above, information and data may also be provided to a physicians' or health-care providers' portal (and device), who may receive alerts about users/patients who have had unusual metrics (e.g., a indicator exceeding a pre-set threshold), and thus be able to review the data and take action, as appropriate.

The atomization chamber and conduit may be cleaned between uses using a cleaning solution, by one or more interior UV light or radiation sources along the chamber and conduit, or combinations thereof.

While the above embodiment has been described for management and treatment of asthma, the present invention also may be used for management and treatment of one or more other conditions, including, but not limited to, COPD, diabetes, cystic fibrosis, and other forms of acute and chronic diseases. The present invention may also be used to provide palliative treatments, such as pain-killers, cannabinoids (e.g., CBD), and the like, especially those taken on a schedule.

In order to provide a context for the various computer-implemented aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, mobile computing devices, microprocessor-based systems, multiprocessor systems, TV set-top boxes and devices, programmable consumer electronics, cell phones, personal digital assistants (PDAs), tablets, smart phones, mobile phones, modular phones, touch screen devices, smart TV, TVs, internet-enabled appliances, internet-enabled security systems, internet-enabled gaming systems, internet-enabled watches; internet-enabled cars (or transportation), network PCs, mini-computers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote process- ing devices (e.g., "cloud computing") linked via a commu- nications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system or computing system environment comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. A client device may comprise a computer-readable medium in the form of vola- tile and/or nonvolatile memory such as read only memory (ROM) and random access memory (RAM) in communica- tion with a processor. The processor executes computer- executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may fur- ther comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmis- sion device, a floppy disk, hard disk drive, CD-ROM, DVD, magnetic disk, memory chip, ROM, RAM, EEPROM, flash memory or other memory technology, an ASIC, a configured processor, CD-ROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infra- red, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C #, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architec- ture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic rou- tines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically con- nected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be con- nected through an output peripheral interface.

Client devices may operate on any operating system capable of supporting an application of the type disclosed herein. Client devices also may support a browser or browser-enabled application. Examples of client devices include, but are not limited to, personal computers, laptop computers, mobile computing devices, personal digital assistants, computer notebooks, hand-held devices, cellular phones, mobile phones, modular phones, smart phones, pagers, digital tablets, Internet appliances, and other proces- sor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A device, comprising:

a housing with an exterior and an interior;

an opening in the housing, said opening configured to receive a pod containing a substance;

a first piezoelectric transducer configured to nebulize some or all of the substance when the pod is inserted into the opening;

an inhalation mouthpiece or mouth port in or on the housing, configured to emit the nebulized substance to a user; and an exhalation mouthpiece or mouth port in or on the housing, configured to receive and direct exhaled breath of the user to a second transducer, said second transducer configured to detect one or more properties of the exhaled breath;

wherein the inhalation mouth port or mouthpiece is separate from the exhalation mouth port or mouthpiece, and the inhalation mouthpiece or mouth port and the exhalation mouthpiece or mouth port do not share any portion of a fluid passageway; and wherein the exhaled breath does not come into contact with the first piezoelectric transducer.

2. The device of claim 1, wherein the device provides both an inhalation function with a first fluid passageway via the inhalation mouthpiece or mouth port, and an exhalation function with a second fluid passageway via the exhalation mouthpiece or mouth port, wherein the first fluid passageway is separate from the second fluid passageway.

3. The device of claim 1, wherein the exhalation mouthpiece or mouth port is on the housing and the exhaled breath does not enter the interior of the housing.

4. The device of claim 1, wherein the second transducer measures pressure.

5. The device of claim 4, wherein the device with exhalation mouthpiece or mouth port and second transducer is configured to act as a spirometer.

6. The device of claim 1, further comprising an ejection button configured to eject the pod from the opening when the ejection button is pressed.

7. The device of claim 1, further comprising a peristaltic pump in the interior of the housing, said pump in fluid communication with an interior of the pod when the pod is inserted.

8. The device of claim 1, wherein the exhalation mouthpiece or mouth port is slidingly or rotatably mounted on the housing.

9. The device of claim 1, further comprising a control board, a battery, and a wireless communication chip.

10. The device of claim 1, wherein the device is portable and hand-held.

* * * * *